(12) United States Patent
Yamka et al.

(10) Patent No.: US 9,848,622 B2
(45) Date of Patent: Dec. 26, 2017

(54) COMPOSITIONS AND METHODS FOR ENHANCING IMMUNE SYSTEM OF FELINES

(75) Inventors: Ryan Michael Yamka, Topeka, KS (US); Kim Gene Friesen, Carthage, IN (US); Steven Curtis Zicker, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 0 days.

(21) Appl. No.: 12/876,451

(22) Filed: Sep. 7, 2010

(65) Prior Publication Data

US 2011/0059138 A1   Mar. 10, 2011

Related U.S. Application Data

(62) Division of application No. 12/528,153, filed as application No. PCT/US2008/054789 on Feb. 22, 2008.

(60) Provisional application No. 60/891,171, filed on Feb. 22, 2007.

(51) Int. Cl.
| | |
|---|---|
| *A23K 50/40* | (2016.01) |
| *A23K 20/174* | (2016.01) |
| *A23K 20/105* | (2016.01) |
| *A23K 20/142* | (2016.01) |
| *A23K 20/158* | (2016.01) |
| *A23K 20/20* | (2016.01) |

(52) U.S. Cl.
CPC ............ *A23K 50/40* (2016.05); *A23K 20/105* (2016.05); *A23K 20/142* (2016.05); *A23K 20/158* (2016.05); *A23K 20/174* (2016.05); *A23K 20/30* (2016.05); *A23V 2002/00* (2013.01)

(58) Field of Classification Search
None
See application file for complete search history.

(56) References Cited

U.S. PATENT DOCUMENTS

| | | |
|---|---|---|
| 6,517,877 B2 | 2/2003 | Gannon |
| 8,496,981 B2 | 7/2013 | Zicker et al. |
| 8,921,422 B2 | 12/2014 | Kelley |
| 2005/0271603 A1 | 12/2005 | Krammer |
| 2007/0037885 A1 | 2/2007 | Edwards |

FOREIGN PATENT DOCUMENTS

| | | |
|---|---|---|
| GB | 2367489 | 4/2002 |
| WO | WO00/44375 | 8/2000 |
| WO | WO00/72698 A1 | 12/2000 |
| WO | WO2005/006877 A1 | 1/2001 |
| WO | WO2004/080196 A2 | 9/2004 |
| WO | WO 2004/095940 | 11/2004 |
| WO | WO 2006/072084 | 7/2006 |
| WO | WO2006/074089 A2 | 7/2006 |

OTHER PUBLICATIONS

Official Publication of Association of American Feed Control Officials (2005, pp. 131-140).*
Baker & Czarnecki-Maulden, 1991 Annu. Rev. Nutr. 11:239-63.
Tang, Children's Food, 1st Ed., China Light Industry Press, May 2003, p. 129 (Cited in Chinese Search Report Feb. 27, 2014).

* cited by examiner

*Primary Examiner* — Aradhana Sasan

(57) ABSTRACT

Compositions and methods useful to enhance the development of the immune system of a growing animal are disclosed.

20 Claims, No Drawings

COMPOSITIONS AND METHODS FOR ENHANCING IMMUNE SYSTEM OF FELINES

CROSS-REFERENCE TO RELATED APPLICATIONS

This application is a divisional of U.S. application Ser. No. 12/528,153 filed on Aug. 21, 2009, which is a US filing under 35 USC 371 of International Application No. PCT/US2008/054789 filed on Feb. 22, 2008, which claims the benefit of U.S. Provisional Application No. 60/891,171, filed on Feb. 22, 2007, the contents of which are incorporated herein by reference.

FIELD OF THE INVENTION

The present invention relates to compositions and methods for enhancing the immune system of mammals.

BACKGROUND OF THE INVENTION

Commercially available pet foods, e.g., cat food, include compositions specially formulated to address many different nutritional needs. These include, for example, formulations designed for different breed types, sizes and body conditions. They also include formulations designed to address the nutritional needs of animals in the different stages of their life cycle. Despite the availability of such pet food formulations, however, there is a need to develop formulations and methods to address other aspects of an animal's health.

Pets are constantly exposed to pathogens. Failure to respond to those pathogens may result in chronic illness and death. Response to pathogens may be inhibited by an animal's diet, preventing an adequate immune response. Thus compositions and methods are needed to enhance an animal's immune response against challenges by pathogens.

The incidence of many infectious diseases in cats has been reduced greatly through the use of vaccines. Vaccines are not 100% effective, as some cats vaccinated against a particular disease will not be immunized against that disease. Thus there is a need to develop compositions and methods to increase the efficacy of vaccines, and to enhance a feline's immune response when challenged with an antigen.

SUMMARY OF THE INVENTION

In certain aspects, the present invention relates to compositions that are useful to enhance the immune system or immune response of an animal when challenged with an antigen.

The present invention includes Composition 1.0, a pet food composition useful to enhance immune function in an animal comprising:
- about 200 to about 1200 IU/kg vitamin E;
- about 50 to about 500 ppm vitamin C;
- about 0.1% to about 0.7% EPA; and
- about 0.1% to about 0.5% DHA.

The present invention also includes the following compositions:

1.1 Composition 1.0 comprising about 0.1% to about 0.5% DHA, e.g., about 0.2% to about 0.4%, e.g., about 0.2, about 0.3, or about 0.4%;

1.2 Composition 1.0 or 1.1 comprising about 200 to about 1200 IU/kg vitamin E, e.g., about 500 IU/kg to about 1100 IU/kg, about 700, about 800, about 900, or about 1000 IU/kg;

1.3 Any of the preceding compositions comprising about 50 to about 500 ppm vitamin C, e.g., about 100 to about 400 ppm Vitamin C, e.g., about 150, about 175, about 200, or about 225 ppm;

1.4 Any of the preceding compositions comprising about 100 ppm to about 500 ppm carnitine, e.g., about 200, about 300, or about 400 ppm;

1.5 Any of the preceding compositions comprising about 2.5 g/1000 kcal to about 7 g/1000 kcal lysine;

1.6 Any of the preceding compositions comprising about 2400 ppm to about 7500 ppm choline, e.g., about 3000, about 4000, about 4500, about 4600, about 4625, about 4650, about 4700, about 5000, or about 6000 ppm;

1.7 Any of the preceding compositions comprising about 0.1% to about 0.6% EPA, e.g., about 0.2%, about 0.3%, about 0.4%, or about 0.5%;

1.8 Any of the preceding compositions comprising about 50 ppm to about 200 ppm manganese;

1.9 Any of the preceding compositions comprising about 0.5% to about 1.6% methionine, e.g., 0.8% to about 1.6% methionine, e.g., about 1.3 or about 1.4% methionine.

1.10 Any of the preceding compositions further comprising:
- 0 to about 90% by weight of carbohydrates;
- about 5% to about 70% by weight of protein;
- about 2% to about 50% by weight of fat;
- about 0.1% to about 20% by weight of total dietary fiber;
- 0 to about 15%, preferably about 2% to about 8%, by weight of vitamins, minerals, and other nutrients, in varying percentages which support the nutritional needs of the animal.

1.11 Composition 1.10 comprising about 5% to about 55%, by weight of carbohydrates;

1.12 Composition 1.10 or 1.11 comprising about 20% to about 60%, by weight of protein, e.g., about 30 to about 55%;

1.13 Any one of compositions 1.10-1.12 comprising about 5% to about 40%, by weight of fat, e.g., at least about 8% or about 9% to about 40% fat;

1.14 Any one of compositions 1.10-1.13 comprising about 1% to about 11%, by weight of total dietary fiber;

1.15 Any of the preceding compositions comprising about 1000 to about 4000 ppm taurine;

1.16 Any of the preceding compositions comprising about 0.5% to about 6% linoleic acid, e.g., about 2.5% to about 5%;

1.17 Any of the preceding compositions comprising about 1% to about 3% total n−3 fatty acids, e.g., about 1.3%, about 1.4%, about 1.5%, or about 1.6%.

1.18 Any of the preceding compositions comprising about 1% to about 6% total n−6 fatty acids, e.g., about 3% to about 5%, about 3.5%, or about 4%.

The compositions of the present invention may be a wet, dry, or semi-dry food.

The present invention includes Method 2.0, a method to enhance the neurologic development of a feline comprising administering to the feline any one of compositions 1.0-1.18.

The present invention also includes the following methods:

2.1 Of method 2.0 wherein the feline is a kitten
2.2 Of method 2.0 or 2.1 wherein the feline is born of a queen fed any one of compositions 1.0-1.18 during pregnancy.
2.3 Of method 2.2 wherein the feline is in utero.
2.4 Of method 2.2 wherein the queen is fed any one of compositions 1.0-1.18 prior to pregnancy.
2.5 Of method 2.2 or 2.4 wherein the queen is fed any one of compositions 1.0-1.18 for a majority of the pregnancy duration.
2.6 Of any one of methods 2.2-2.5 wherein the queen is fed compositions consisting essentially of any one of compositions 1.0-1.18 prior to and during pregnancy.
2.7 Of any one of the preceding methods wherein the kitten is fed any one of compositions 1.0-1.18 prior to weaning, e.g., while still nursing.
2.8 Of any one of the preceding methods wherein the kitten is fed any one of compositions 1.0-1.18 post weaning.
2.9 Of method 2.8 wherein the kitten is fed food compositions consisting of any one of compositions 1.0-1.18.
2.10 Of any one of the preceding methods wherein an effective amount of the composition is administered to the animal.
2.11 Of any one of the preceding methods wherein the composition is administered to the animal for an effective amount of time.

Other features and advantages of the present invention will be understood by reference to the detailed description of the examples that follow.

DETAILED DESCRIPTION OF THE INVENTION

It is contemplated that the invention described herein is not limited to the particular methodology, protocols, and reagents described as these may vary. It is also to be understood that the terminology used herein is for the purpose of describing particular embodiments only, and is not intended to limit the scope of the present invention in any way.

Unless defined otherwise, all technical and scientific terms used herein have the same meanings as commonly understood by one of ordinary skill in the art to which this invention belongs. In addition, all references cited herein are hereby incorporated by reference in their entireties. In the event of a conflict in a definition in the present disclosure and that of a cited reference, the present disclosure controls.

As used herein and in the appended claims, the singular forms "a", "an", and "the" include plural reference unless the context clearly dictates otherwise.

The present invention relates to any animal, preferably a mammal, more preferably a companion animal. The term "companion animal" refers to any animal that lives in close association with humans and includes, but is not limited to, canines and felines of any breed. It is contemplated herein, however, that any animal whose diet may be controlled by humans may benefit from feeding the formulations disclosed herein. These animals may include, for example, domesticated farm animals (e.g., cattle, horses, swine, etc.) as well as undomesticated animals held in captivity, e.g., in zoological parks and the like. Preferably, the animal is a feline, either a kitten, or adult cat.

As used herein, "an amount effective to" or "an effective amount" to achieve a particular result, and like terms, refer to that amount of a compound, material or composition as described herein that may be effective to achieve a particularly desired biological result. As contemplated herein, such results include, for example, enhancement of neurologic development, bone and joint health, immune function and/or promotion of a healthy body composition of an animal, either while developing in utero and/or during its growth stage after birth, e.g., up to 6 months, 9 months, 12 months, or 15 months after birth. Such effective activity may be achieved, for example, by administration of compositions of the present invention to the dam of said animal while the animal is in utero or nursing, as well as by direct administration to the animal during its growth stage.

As used herein, the "enhancement" of a particular biological process or body condition in a growing animal such as described herein refers to an improvement in the biological process or body condition of a growing animal compared to a control animal. Improvement in such a process or condition may be determined by one of skill in the art. Immune function may be determined in an animal by assaying antibody titers in response to vaccination and comparing to control animals, where an increase in antibody titer compared to controls is indicative of an enhancement in adaptive immune function.

As used herein, "enhancement of the development of a growing animal" or "enhanced growth" and like terms refer to an overall improvement in one or more biological processes and/or the body condition of a growing animal, including but not limited to, biological processes central to the growth and development of an organism, including, but not limited to, the biological processes described herein, e.g., bone and joint health, neurologic and immune system development and body weight gain (e.g., increase in lean muscle mass instead of adipose tissue).

The "growth" life stage of an animal refers to the period from birth or weaning (approx 8 weeks of age) to about 1 year of age.

As used herein, the term "kitten" refers to an immature feline, typically between the ages of birth and 12 months.

"Essential amino acids" as used herein refers to those amino acids that cannot be synthesized de novo by an organism and thus must be supplied in the diet. It is understood by one of skill in the art that the essential amino acids vary from species to species, depending upon the organism's metabolism. For example, it is generally understood that the essential amino acids for dogs and cats (and humans), are phenylalanine, leucine, methionine, lysine, isoleucine, valine, threonine, tryptophan, histidine and arginine. In addition, taurine, while technically not an amino acid but a derivative of cysteine, is an essential for cats. A balanced diet can provide all the essential amino acids, however, there are certain essential amino acids that are more critical, as a diet deficient in one of them will limit the usefulness of the others, even if the other essential amino acids are present in sufficient quantities.

As understood by one of skill in the art, a "limiting amino acid" refers to an amino acid which if present in insufficient quantities in a diet, results in the limitation in usefulness of other essential amino acids, even if the other essential amino acids are present in otherwise large enough quantities. Lysine is the limiting essential amino acid in the compositions disclosed herein. Thus, the remaining essential amino acids are quantitatively formulated or "balanced" in relationship to the amount of lysine determined critical to affect the desired biological result. As used herein, "balanced amino acids" refers to the relationship of the essential amino acid lysine to energy to assure optimal animal growth and development.

"Essential nutrients" as used herein refers to nutrients required for normal body functioning that cannot be synthesized by the body. Categories of essential nutrient include vitamin dietary minerals, fatty acid, and amino acid. It is understood by one of skill in the art that the nutrients deemed essential varies from species to species, depending upon the organism's metabolism. For example, essential nutrients for dogs and cats include Vitamins A, D, E, K, B1, B6 B12, riboflavin, niacin, pantothenic acid, folic acid, calcium, phosphorous, magnesium, sodium, potassium, chlorine, iron, copper, zinc, manganese, selenium and iodine. Choline, generally regarded as a B complex vitamin, may be included among the semi-essential nutrients.

Carnitine, also known as L-carnitine, (levocarnitine) is a quaternary ammonium compound synthesized from the amino acids lysine and methionine and is responsible for the transport of fatty acids from the cytosol into the mitochondria.

The immune response of various animals, such as mammals and felines is well known in the art. An immune response is generally the mechanisms within an organism that protects against disease, e.g., by identifying and killing pathogens and tumor cells. Immune responses may be classified into various response types, e.g., humoral or cell-mediated response, and innate and adaptive response. Thus, immune responses may be humoral innate responses, cell-mediated innate response, cell-mediated adaptive response, and cell-mediated adaptive response, and combinations thereof. It is well known that these responses may occur concurrently when an animal is challenged, e.g., with a pathogen. For example, the complement cascade of the innate humoral immune response may recruit T and B cells, which form the basis of cell-mediated adaptive immunity, and complement may be recruited by the adaptive immune system.

Without being limited to any theories or particular modes of action, the present invention is based on the surprising discovery that the diet of an animal may enhance the animal's immune response to antigens, e.g., pathogens or vaccines. Addition of certain ingredients to pet food compositions and administration of these compositions to animals can enhance the immune system of a growing animal. Additionally, the addition of certain ingredients to pet food compositions and administration of these compositions to dams during pregnancy can enhance the immune system of the offspring thereof.

The present invention contemplates that the immune response of a feline may be enhanced or augmented against any number of antigens, including pathogens and vaccines. Felines may be vaccinated against any number of diseases or conditions, including feline panleukopenia, feline herpesvirus-1, feline calicivirus, feline leukemia virus, rabies, chlamydiosis, feline infectious peritonitis, *Bordetella bronchiseptica* infection, dermatophytosis, giardiasis, etc. Thus the present invention contemplates an improved method of establishing enhanced adaptive humoral immunity, e.g., against a pathogen comprising the methods of the present invention, and immunizing an animal against a pathogen with a vaccine for the pathogen. Enhanced immune function in an animal may be characterized as an immune response which demonstrates greater antibody or cell-mediated response upon antigen challenge than control animals.

As contemplated herein, the compositions of the present invention comprise nutritionally complete and balanced animal feed compositions. Such compositions include, among other nutrients and ingredients, recommended healthful amounts of protein, carbohydrate and fat. "Nutritionally complete and balanced animal feed compositions", as well as nutrients and ingredients suitable for animal feed compositions, and recommended amounts thereof, are familiar to one of skill in the art (see, for example, National Research Council, 2006 Nutritional Requirements for Dogs and Cats, National Academy Press, Washington D.C. or the Official Publication of the Association of American Feed Control Officials, Inc. Nutrient Requirements for Dogs and Cats 2006).

It is contemplated herein that the compositions disclosed herein may also comprise antioxidants, additives, stabilizers, thickeners, flavorants, palatability enhancers and colorants in amounts and combinations familiar to one of skill in the art. "Antioxidants" refers to a substance that is capable of reacting with or decreasing the production of free radicals and neutralizing them. Examples include, but are not limited to, beta-carotene, selenium, coenzyme Q10 (ubiquinone), lutein, tocotrienols, soy isoflavones, S-adenosylmethionine, glutathione, taurine, N-acetylcysteine, vitamin E, vitamin D, vitamin C, flavanoids, anthocyanindins, and lipoic acid.

While foods of any consistency or moisture content are contemplated, preferably the compositions of the present invention may be, for example, a wet, semi-dry or dry animal food composition. "Wet" food refers to food which is sold in cans or foil bags and has a moisture content of about 70 to about a 90%. "Dry" food refers to compositions with about 5 to about 15% moisture content and is often manufactured in the form of small bits or kibbles. Semi-dry compositions refer to compositions having about 15% to about 70% moisture. Also contemplated herein are compositions of intermediate moisture consistency and those that may comprise components of various consistency as well as components that may include more than one consistency, for example, soft, chewy meat-like particles as well as kibble having an outer cereal component and an inner cream component as described in, e.g., U.S. Pat. No. 6,517,877.

The following examples further illustrate the present invention and are not intended to limit the invention. As used throughout, ranges are used as shorthand for describing each and every value that is within the range. Any value within the range can be selected as the terminus of the range. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

Example 1

Formulations to enhance the development of growing animal are disclosed hereinbelow. These compositions are developed taking into account the "ideal protein concept" (Baker and Czarnecki-Maulden, 1991 Annu. Rev. Nutr. 11:239-63).

Foods are developed for the "growth" life stage. These foods include formulations for canine growth and feline growth. The minimum nutrient recommendations for these foods, as well as the targeted values for a prototype food, are listed below in Table 1.

TABLE 1

Key Nutrients for Kitten Formula

| Nutrient | Target | Minimum | Maximum |
|---|---|---|---|
| Protein, % | 45.5 | 30 | 55 |
| Methionine, % | 1.4 | 0.8 | 1.56 |
| Manganese, ppm | 90 | 50 | 200 |
| DHA, % | 0.21 | 0.1 | 0.5 |
| EPA, % | 0.31 | 0.1 | 0.7 |
| Choline, ppm | 4880 | 2500 | 7500 |
| Taurine, ppm | 2380 | 1000 | 4000 |
| Linoleic acid, % | 3.8 | 2.5 | 6 |
| Total n-3 fatty acids, % | 1.35 | 1 | 3 |
| Vitamin E, IU/kg | 900 | 200 | 1200 |
| Vitamin C, ppm | 90 | 50 | 500 |
| Lysine, g/1000 kcal | 4 | 2.5 | 7 |

Example 2

Four foods are used for the study, experimental Formulation X, Commercial A, Commercial A1, and Commercial B. The composition of the foods is presented in Table 2. Commercial A, A1, and B foods are available from commercial sources. Commercial A and A1 are the same brand of food, but produced in different lots.

TABLE 2

Analyzed nutrients of foods fed to queens and kittens

| Nutrient | Formula X | Commercial A | Commercial A1 | Commercial B |
|---|---|---|---|---|
| Crude Protein, % | 41.63 | 41.2 | 36.09 | 35.47 |
| Fat, % | 23.15 | 14.47 | 12.43 | 22.94 |
| Ca, % | 1.23 | 1.12 | 1.50 | 1.06 |
| P, % | 1.11 | 1.11 | 1.19 | 0.96 |
| DHA, % | 0.22 | 0.06 | 0.04 | <0.01 |
| EPA, % | 0.32 | 0.06 | 0.04 | <0.01 |
| Linoleic Acid, % | 3.79 | 1.59 | 1.96 | 1.37 |
| Total n-3 fatty acids, % | 1.47 | 0.34 | 0.25 | 0.53 |
| Total n-6 fatty acids, % | 3.86 | 1.88 | 1.91 | 1.44 |
| Taurine, % | 0.24 | 0.17 | 0.23 | 0.20 |
| Methionine, % | 1.3 | 0.76 | 0.62 | 0.99 |
| Cystine, % | 0.49 | 0.51 | 0.44 | 0.35 |
| Manganese, ppm | 78 | 63 | 77 | 56 |
| Vitamin E, IU/kg | 914 | 35 | 76 | 138 |
| Vitamin C, ppm | 183 | — | — | — |
| Choline, ppm | 4624 | 3010 | 2807 | 3331 |

19 queens are fed Formulation X, or Commercial A for at least 2 weeks prior to conception. Queens are maintained in group lodging until they are confirmed pregnant via palpation, and are then moved to maternity lodging. 32 kittens are produced from queens fed Commercial A, and 16 kittens are produced from queens fed Formulation X. Following birth of kittens, the kittens from queens are kept on same foods until the kittens are weaned.

Following weaning, the 32 kittens produced from queens fed Commercial A were divided as follows: 16 kittens are fed Commercial A1; and 16 kittens are fed Commercial B. Following weaning, the 16 kittens produced from the queens fed Formulation X are maintained on Formulation X.

The 48 kittens are vaccinated against rabies, and anti-rabies antibody titers were determined prior to vaccination, and at 1, 2, 4, 8 and 16 weeks following vaccination.

Results are presented in Table 3. Kittens from queens fed Formula X and continued to feed on Formula X have significantly improved immune response, as measured by increased antibody titer to the rabies vaccination. The antibody titer in kittens is significantly increased when Formula X is fed to queens during gestation and lactation, and to the kittens after weaning during growth.

TABLE 3

Mean antibody titer of kittens in response to rabies vaccination

| | Pre-vaccination | 1 week | 2 weeks | 4 weeks | 8 weeks | 16 weeks |
|---|---|---|---|---|---|---|
| Commercial A dams- Commercial A1 kittens | 0.1 | 0.1 | 22.0 | 43.3 | 47.5 | 25.0 |
| Commercial A dams- Commercial B kittens | 0.1 | 0.2 | 23.4 | 47.0 | 52.8 | 12.5 |
| Formula X dams- Formula X kittens | 0.1 | 0.2 | 26.4 | 62.4 | 63.9 | 37.2 |

The invention claimed is:

1. A method to enhance the immune response of a feline to an antigen, the method comprising:
   administering to the feline in need thereof and to the mother of the feline while the feline is in utero, a pet food composition comprising:
   about 200 to about 1200 IU/kg vitamin E;
   about 50 to about 500 ppm vitamin C;
   about 0.1% to about 0.7% EPA;
   about 2400 ppm to about 7500 ppm choline; and
   about 0.1% to about 0.5% DHA,
   wherein the feline is a kitten born from a queen fed the composition prior to pregnancy and during the pregnancy; and
   wherein the kitten is also fed the composition prior to weaning and post weaning.

2. The method of claim 1, wherein the immune response is a humoral immune response.

3. The method of claim 1, wherein the immune response is an adaptive humoral immune response.

4. The method of claim 3, wherein the adaptive humoral immune response includes the production and release of antibodies against the antigen.

5. The method of claim 1, wherein the antigen is presented in a vaccine.

6. The method of claim 5, wherein the vaccine is feline panleukopenia, feline herpesvirus-1, feline calicivirus, feline leukemia virus, rabies, chlamydiosis, feline infectious peritonitis, *Bordetella bronchiseptica* infection, dermatophytosis, or giardiasis.

7. The method of claim 6, wherein the vaccine is rabies.

8. The method of claim 7, wherein an antibody titer in the kitten is increased as compared to kittens born to queens not administered the pet food composition.

9. The method of claim 1, wherein after weaning an antibody titer in the kitten sixteen weeks after vaccination is 50% to 150% higher as compared to kittens born to queens not administered the pet food composition.

10. The method of claim 9, wherein the vaccine is feline panleukopenia, feline herpesvirus-1, feline calicivirus, feline leukemia virus, rabies, chlamydiosis, feline infectious peritonitis, *Bordetella bronchiseptica* infection, dermatophytosis, or giardiasis.

11. The method of claim 10, wherein the vaccine is a rabies vaccine.

12. The method of claim 1, wherein the pet food composition further comprises an additional antioxidant.

13. The method of claim 12, wherein the additional antioxidant is one or more of beta-carotene, selenium, coenzyme Q10 (ubiquinone), lutein, tocotrienols, soy isoflavones, S-adenosylmethionine, glutathione, taurine, N-acetylcysteine, vitamin D, flavanoids, anthocyanindins, and/or lipoic acid.

14. The method of claim 1, wherein the composition further comprises about 2.5% to about 5.0% linoleic acid.

15. The method of claim 1, wherein the composition further comprises about 2.5 g/1000 kcal to about 7 g/1000 kcal lysine.

16. The method of claim 14, wherein the composition further comprises about 2.5 g/1000 kcal to about 7 g/1000 kcal lysine.

17. The method of claim 1, wherein the composition further comprises about 50 ppm to about 200 ppm manganese.

18. The method of claim 16, wherein the composition further comprises about 50 ppm to about 200 ppm manganese.

19. The method of claim 1, wherein the total amount of n−3 fatty acids in the composition is from about 1% to about 3%.

20. The method of claim 1, wherein the total amount of n−6 fatty acids in the composition is from about 3% to about 5%.

* * * * *